United States Patent [19]
Grases Freixedas et al.

[11] Patent Number: 6,027,939
[45] Date of Patent: Feb. 22, 2000

[54] PROCESS FOR EVALUATING THE GLOBAL CAPACITY OF URINE TO FORM CHALKY RENAL CALCULUS, AND CORRESPONDING KIT

[75] Inventors: Félix Grases Freixedas, Palma de Mallorca; Joan Gabriel March Isern, Binissalem; Antonia Costa Bauza; Laura García Ferragut, both of Palma de Mallorca, all of Spain

[73] Assignee: Universidad de Las Islas Baleares, Baleares, Spain

[21] Appl. No.: 09/142,627

[22] PCT Filed: Dec. 11, 1996

[86] PCT No.: PCT/ES96/00237

§ 371 Date: Sep. 8, 1998

§ 102(e) Date: Sep. 8, 1998

[87] PCT Pub. No.: WO97/33172

PCT Pub. Date: Sep. 12, 1997

[30] Foreign Application Priority Data

Mar. 8, 1996 [ES] Spain ................................. 9600572

[51] Int. Cl.[7] .................................................. G01N 21/29
[52] U.S. Cl. .............................. 436/74; 436/79; 436/164; 436/177; 422/61
[58] Field of Search ................................. 422/61; 436/74, 436/79, 165, 164, 177

[56] References Cited

U.S. PATENT DOCUMENTS

| 4,025,307 | 5/1977 | Randolph et al. . | |
| 4,183,729 | 1/1980 | Randolph | 422/245 |
| 4,399,003 | 8/1983 | Sarig et al. . | |
| 4,921,807 | 5/1990 | Pak . | |
| 5,057,435 | 10/1991 | Denney | 436/79 |
| 5,064,765 | 11/1991 | Karasikov et al. | 436/4 |
| 5,604,103 | 2/1997 | Thomas, Jr. et al. | 435/7.1 |
| 5,629,211 | 5/1997 | Tsutsumi | 436/74 |

FOREIGN PATENT DOCUMENTS 2088743  8/1996  Spain .

OTHER PUBLICATIONS

Grases et al.,1995, Intl Urol Nephrol, 27:653–61.

*Primary Examiner*—Jeffrey Snay
*Attorney, Agent, or Firm*—Klauber & Jackson

[57] ABSTRACT

A process is provided for evaluating the global capacity of urine to form chalky renal calculus, the process comprising the steps of pouring a sample of a recently discharged urine into a container plate bearing, on its inner bottom portion, a cup containing a reaction substrate capable of initiating crystallization of calcium in the sample, allowing the sample to rest; discarding the sample from the container plate, washing the container plate with bidistilled water and discarding the water, adding a diluted HCl solution (2.3N) and spreading it over the entire surface of the substrate contained in the cup, adding an aqueous sodium acetate solution (5% w/v) and an indicating solution of ARSENAZO III (0.1% w/v) and mixing the acetate solution and the indicating solution for 15 seconds, to obtain a stained reaction mixture which can be qualitatively and quantitatively evaluated. A kit for carrying out this process is also provided.

2 Claims, 2 Drawing Sheets

PROCESS FOR EVALUATING THE GLOBAL CAPACITY OF URINE TO FORM CHALKY RENAL CALCULUS, AND CORRESPONDING KIT

TECHNICAL FIELD OF THE INVENTION

The present invention is inserted in the field of study of the risk of calcic renal lithiasis, specifically on the development of a kit type system that allows the evaluation of the capacity of forming calcic crystals in a urine sample of any individual.

PRIOR ART OF THE INVENTION

The formation of renal calculus, as it is known, is due in practically all cases to the unfortunate combination of several factors. These factors may be classified in two large groups: I) factors inherent to the composition of urine. II) factors related to the morpho-anatomy of the kidney.

Urine is a metastable medium where there are normally different substances that may crystallize forming calculus (substances that are found in a state of supersaturation). Whether or not these substances crystallize depends on the degree of supersaturation, the presence of promoting substances (heterogeneous nucleants) and the presence of crystallization inhibitors.

The presence of cavities with a low urodynamic efficacy and that, therefore, keep the urine retained for long periods of time, and the alterations of the epithelium that covers the renal papilla (reduced or eliminated layer of glycosaminoglykanes, necrosis, . . . ) are factors linked to the renal structure that favor the formation of renal calculus.

Normally, the existence of factors belonging to both groups is necessary for the formation of renal calculus. The test that is presented precisely makes it possible to evaluate in a very simple manner the capacity that specific urine has to crystallize calcic salts, in such a way that the urine of a healthy individual would not give rise to growth of calcic salt crystals, while urine tending to form renal calculus (very supersaturated and/or with a significant inhibition deficit and/or abundant heterogeneous nucleants) would produce calcic salt crystals.

As bibliographic references closely related to the object of the present invention, the following may be cited: J. M. Baumann. How reliable are the measurements of crystallization conditions in urine? Urol. Res. 16, 133–135 (1988); J. M. Baumann. How to measure crystallization conditions in urine: A comparison of 7 methods. Report from a workshop held on Nov. 28, 1987 in Basle. Urol. Res 16, 137–142 (1988); F. Grases, O. Söhnel. Mechanism of oxalocalcic renal calculi generation, Int. Urol. Nephrol. 25, 209–214 (1993); F. Grases, A. Costa-Bauzá, J. G. March, O. Söhnel, Artificial simulation of renal stone formation. Influence of some urinary components. Nephron 65, 77–81 (1993); F. Grases, A. Costa-Bauzá, J. G. March. Artificial simulation of the early stages of renal stone formation. Brit. J. Urol. 74, 298–301 (1994).

ES-A-2088743 discloses a method for the determination of the inhibitive capacity of crystallization in human urine samples and the corresponding kit therefor.

The cited method essentially comprises the following operations:

(a) introducing the urine sample in a container that includes a substrate or flat solid surface that initiates crystallization, at 37° C. for about 5–6 hours; (b) removing the substrate containing the crystals and dissolving them in an acid medium; (c) evaluating the amount of calcium contained in said crystals.

The kit used to carry out this method comprises (1) a small vessel containing a substrate (2); (3) a container of the urine to be analyzed; (4) a container where the other container (1) is inserted; (5) a test tube type container, in which the dissolving of the crystals deposited in substrate (2) takes place.

Grases, F. et al (1995) International Urology and Nephrology 27: 653–661 discloses a similar process as that of ES-A-2088743.

Fernádndez-Dapica, M. P. et al. (1994) Arthritis & Rheumatism 370: s143 discloses a method for analyzing the calcium phosphate contents of synovial liquids using ARENAZO III colorimetrical assay. This method is inadequate for providing a simplified process for evaluating the capacity of urine as that of ES-A-2088743 inasmuch the method of Fernández-Dapica implies digesting the samples of synovial fluid with NaOH at high temperatures (about 100° C.). U.S. Pat. No. 4,921,807 discloses a method and apparatus for maintaining urine specimens wherein thymol is added to the specimens for the purpose of preventing bacterial contamination/deterioration during storage and/or transport thereof.

The applicant has continued doing research on this method and kit, managing to improve both, so as to achieve a kit with easy industrial distribution and simplified use by the user in his home, as opposed to the need to carry out specialized laboratory tests.

DETAILED DESCRIPTION OF THE INVENTION

As indicated in the title, the present invention refers to a process of evaluation of the overall capacity of urine to form calcic renal stones and the corresponding kit therefor.

When an unprotected and unrenewed surface comes in contact with urine, sooner or later those substances that are supersaturated and whose inhibition is deficient end up crystallizing on it. The ease with which this crystallization takes place depends on how favorable the combination of factors that stimulate it is. Thus, by using a suitable surface it is possible to calculate a time period for which urine with a normal composition does not crystallize, while lithogenous urine gives rise to the growth of calcic salts on the same. Detection of the calcium produced in these conditions is carried out by using a calorimetric reaction. In short, there are two reactions that take part in the process: a precipitation reaction and a complexation reaction.

Precipitation reaction: $Ca^{2+} + Oxalate/Phosphate > Oxalate/Calcium\ phosphate$ Complexation reaction: Redissolved Ca (II)+2,7-Naphthalenedisulfonic acid, 3,6-bis((2-arsonophenyl)azo)-4,5-dihydroxy (ARSENAZO III). →Blue complex pH=4.3

In order to carry out the process of the present invention, a kit that is represented in FIG. 1 and that essentially comprises a vessel containing thymol as a sterilizing agent (1), within which there is a reaction cup (2), where the reaction substrate (3) is located, has been designed.

In order to carry out the test the following reagents (prepared in bidistilled water with reagents of maximum purity) are needed.

Reaction units

Aqueous solution of 2.3 N hydrochloric acid

Aqueous solution of anhydrous sodium acetate 5% (w/v)

Aqueous solution of ARSENAZO III, 0.1% (w/v)

All of the solutions must be kept between 2 and 8° C. They must be brought to room temperature (20 to 30° C.) 30 minutes before they are used. The hydrochloric acid and ARSENAZO III solutions are stable for the 90 days following their preparation when they are kept between 2 and 8° C. The sodium acetate solution is stable for 30 days when it is kept between 2 and 8° C.

The reaction units must be kept closed and at room temperature (20 to 30° C.).

The collecting of the sample will be done in a sterile 100 mL bottle. The urine must be discharged before breakfast, if possible the first urination in the morning and if not the following urination but always before breakfast.

Neither additives nor preservatives should be added to the collected sample.

It is essential that the test is started with recently discharged and even warm urine in order to prevent precipitation reactions from being produced due to cooling of the urine. Cooled or frozen samples must never be used.

The analytic process of the invention involves a series of steps that are outlined in FIG. 2 and that are specified in detail hereinafter.

1. —Label the reaction unit with the patient's identification.
2. —Pour 40 mL of recently discharged urine on the plate. Make sure that the reaction cup is filled with urine. Cover the container plate.
3. —Allow the sample to rest for:
   a) 6 h at 37° C. or 12 h at room temperature (20 to 30° C.)
   b) 24 h at room temperature (20 to 30° C.)
4. —Discard the contents of the containing plate.
5. —Carefully wash the plate with 50 mL of bidistilled water. Do not pour the water directly on the reaction cup. Stir for 5 seconds with gentle stirring movement. Discard the water.
6. —Add 400 µL of the acid solution to the reaction cup.
7. —Spread the solution over the entire surface by means of gentle but continuous movement with a plastic spatula. Prolong this operation for about 2 minutes.
8. —Add 2.8 mL of the acetate solution to the reaction cup.
9. —Add 150 µL of the ARSENAZO III solution to the reaction cup.
10. —Mix with the spatula while the reaction is being completed (about 15 sec.)
11. —Interpret the result qualitatively and/or quantitatively.

It is recommended that a negative control be prepared daily as a contrast in order to verify the test result. The negative control is prepared on the cup of one new reaction unit to which the previous protocol as of step 6 will be applied.

Once the test has ended, a stained solution is obtained. In terms of the color the result is evaluated qualitatively as positive or negative.

Negative non-lithogenous urine will have a pink color similar to that of the negative control.

Positive lithogenous urine will have a blue color, whose shade may vary from violet to blue.

Urine with a lithogenous risk close to cut-off, that is to say, to the sensibility limit of the test, will have a pink color with a slight bluish tone.

In those cases in which it is considered convenient, clinical laboratory analysis may proceed a quantitative interpretation of the obtained results. In order to do so, it suffices to determine the absorbency of the stained solution at 650 nm in comparison to a target of bidistilled water using dishes of 1 cm of optical path. In this case the result will be expressed in the concentration of calcium (µg/mL) and will be calculated in accordance with the following equation:

$$[Calcium]_m = A_m \times [Calcium]_{std}/A_{std}$$

wherein: $[Calcium]_m$ is the concentration of calcium of the sample.

$A_m$ is the absorbency of the sample.

$[Calcium]_{std}$ is the concentration of calcium of a standard solution.

$A_{std}$ is the absorbency of a standard solution.

The concentration of calcium in the stained solution may also be directly determined by means of atomic absorption spectrometry (AAS) or inductively coupled plasma-atomic emission spectrometry (ICP-AES).

For non-lithogenous urine the concentration of calcium in the stained solution will be between 0 and 2 µg/mL.

For lithogenous urine the concentration of calcium in the stained solution will be between 3 and 30 µg/mL. Crystallizations above 30 µg/mL have rarely been obtained.

For urine with a lithogenous risk close to cut-off, that is to say, the sensitivity limit of the test, the concentration of calcium in the stained solution will be between 2 and 3 µg/mL.

The results obtained by applying the test show an excellent discrimination between the group of healthy individuals and the group of patients with a significant lithiasic activity and altered urine, which shows the usefulness of the test to evidence the existence of urinary disorders that may lead to the formation of renal calculus. It is obvious that if one wishes to specifically detect a specific disorder, it will be necessary to carry out a more detailed urinalysis.

It is important to point out that it may happen that clearly lithogenous urine may belong to an individual who has never formed renal calculus, due to the fact that the morpho-anatomic factors of the kidney are especially oriented towards avoiding the formation of solid concretions, for example, as a result of the existence of a particularly well developed layer of glycosaminoglykanes (nonsticking layer). The contrary may also happen, wherein, totally normal urine from a lithogenous point of view, belongs to a clearly lithiasic individual, which must be attributed to a situation wherein the morpho-anatomic factors of the kidney are clearly altered, for example, by the presence of significant papillary necrosis, that would favor the formation renal calculus. It must also considered that the lithogenous activity of an individual is not the same every day of the year. There are seasons, such as the summer for example, especially suited to the formation of renal calculus, and the influence of cycles, such as the menstrual cycle which affects the elimination of citrate, must also be considered. Therefore, it is obvious that for a lithiasic individual there may be periods when his urine has no lithiasic activity and others when it has lithiasic activity. The application of the test will undoubtedly allow the detection of said periods.

In short, the proposed test makes it possible to carry out an overall evaluation of the urinary risk to form calcic calculus. If the result is positive, it will indicate a clear predisposition of the urine to form calcic calculus, in such a way that if one wishes to know more exactly the altered urinary factor(s) (hypercalcuria, hypocyturia . . . ) it will be necessary to carry out a more complete urinalysis. If the result of the test is negative and calcic calculus are formed in the absence of urinary infection, it is a clear indication that the alteration that produces them basically arises from the morpho-anatomic factors of the kidney.

Therefore, the application of the test will be of special interest for:

1) Rapid sampling of patients with calcic lithiasis for the purpose of detecting those individuals who have altered urine and that must be subjected to a more complete urinalysis.
2) Identification of the predisposition of the formation of calcic renal calculus in individuals with an important lithogenous risk factor (for example, in cases of the existence of direct family case histories.)
3) Evaluation of the efficacy of a specific corrective therapy of the urinary lithogenous risk.
4) Detection of periods of marked lithogenous activity.

EMBODIMENTS OF THE INVENTION

Figure 1:
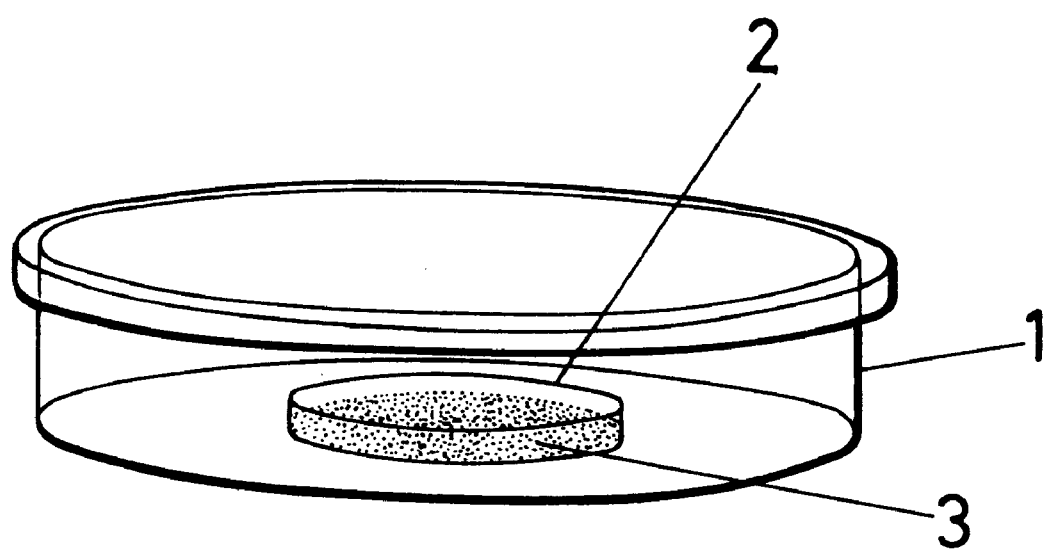
FIG. 1 represents the kit of the present invention, wherein (1) corresponds to the container containing thymol, (2) corresponds to the cup and (3) corresponds to the reaction substrate.
Figure 2:
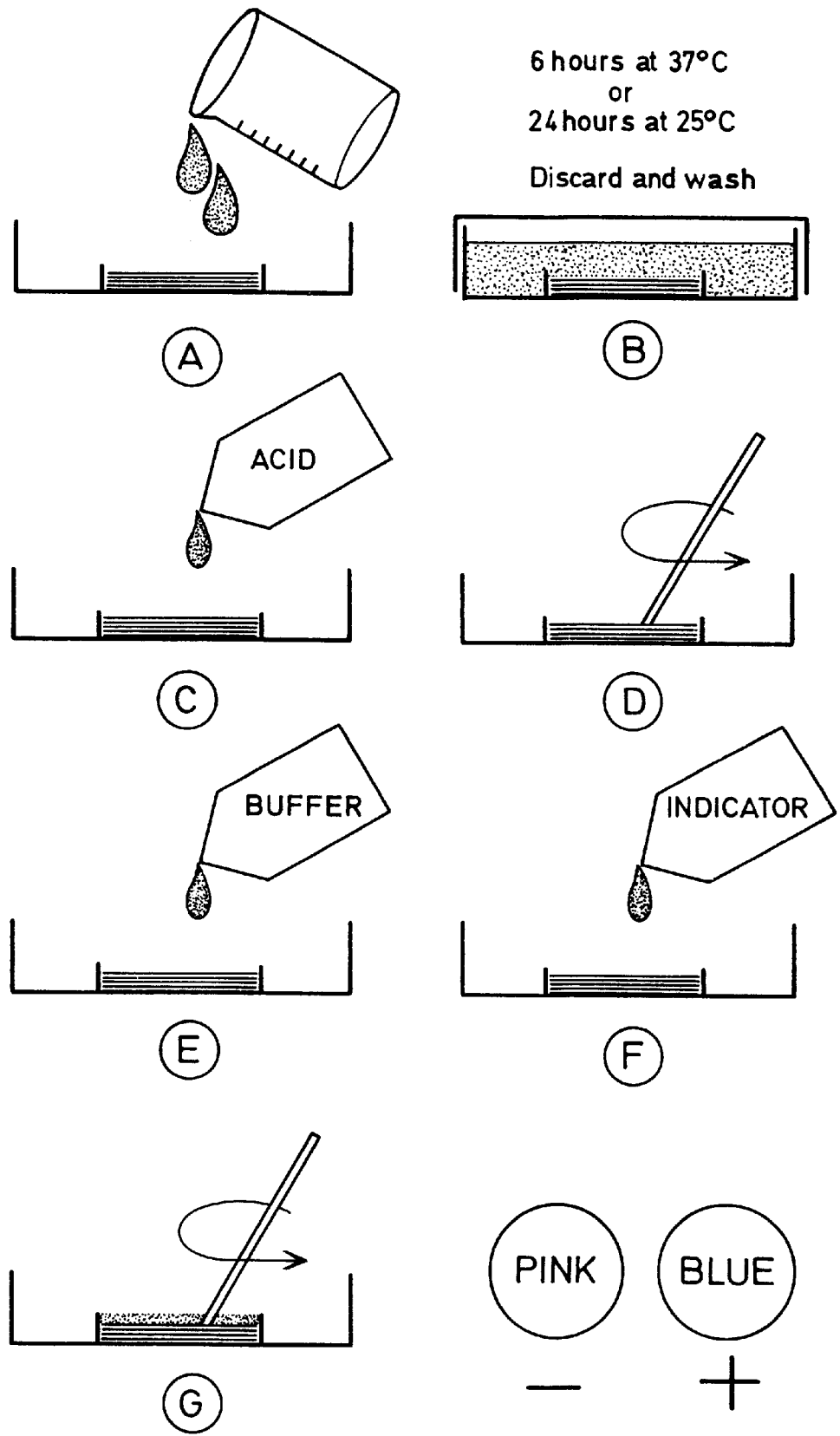
FIG. 2 represents an illustrative diagram of the test method of the present invention.

The present invention is additionally illustrated by means of the following Examples which are not restrictive of the scope hereof.

EXAMPLE 1

40 mL of recently discharged urine were taken and deposited in a container plate making sure that the cup was filled. It was covered and allowed to rest for 6 hours at 37° C.

Once this time has gone by, the plate was carefully washed with 50 mL of bidistilled water with the precaution of not pouring it directly on the reaction cup, it was stirred gently for 5 seconds and the water was discarded.

Then 400 μL of an aqueous solution of 2,3N hydrochloric acid were added and extended carefully with a plastic spatula for 2 minutes. Afterwards, 2.8 mL of an aqueous solution of anhydrous sodium acetate 5% (w/v) and 150 μL of ARSENAZO III were added. It was mixed with the spatula for 15 seconds and then the formation of the pink color was observed, indicating an non-lithogenous urine.

EXAMPLE 2

The process described in Example 1 was repeated, using recently discharged urine from another subject. The urine was kept in contact with the substrate for 12 hours at room temperature.

The stain at the end of all the stages of the process was blue, indicating a lithogenous urine.

We claim:

1. A process for evaluating the global capacity of urine of a human individual to form chalky renal calculus, the process comprising the steps of pouring a sample of a recently discharged urine into a container plate with a reaction substrate capable of initiating crystallization of calcium present in the sample, wherein the process further comprises pouring 40 ml of the sample into the container plate, making sure that a cup located on an inner bottom portion within the container plate and containing the reaction substrate is filled, covering the container plate and allowing the sample to rest for a period of time selected from one of 6 hours at 37° C., 12 hours at room temperature, or 24 hours at room temperature;

discarding the sample from the container plate, washing the container plate with 50 ml of bidistilled water and discarding the water;

adding 400 $\mu^1$ of an diluted HCl solution (2.3N) and spreading it over the entire surface of the substrate contained in the cup, adding 150 $\mu^1$ of an aqueous sodium acetate solution (5% w/v) and 150 $\mu^1$ of an indicating solution of 2,7-Naphthalenedisulfonic acid, 3,6-bis((2-arsonophenyl)azo)-4,5-dihydroxy (0.1% w/v), and mixing the acetate solution and the indicating solution for 15 seconds, whereby a stained reaction mixture for qualitative and quantitative evaluation is obtained.

2. A kit for carrying out the process of claim 1 for evaluating the capacity of forming calcic crystals in a urine sample of a human individual, the kit comprising at least one reaction unit comprising a container plate for receiving the urine sample and containing thymol as a sterlizing agent provided with a cover, the container plate having an inner bottom portion whereon a cup containing a reaction substrate is located;

an aquoeus solution of 2,3 N hydrochloric acid;

an aquoeus solution of anhydrous sodium acetate 5% (w/v); and an aqueous solution of 2,7-Naphthalenedisulfonic acid, 3,6-bis((2-arsonophenyl)azo)-4,5-dihydroxy, 0.1% (w/v).

* * * * *